US008756076B2

(12) United States Patent
Griffin et al.

(10) Patent No.: US 8,756,076 B2
(45) Date of Patent: Jun. 17, 2014

(54) HIPAA-COMPLIANT THIRD PARTY ACCESS TO ELECTRONIC MEDICAL RECORDS

(75) Inventors: Jane Griffin, Lee's Summit, MO (US); Marsha Laird-Maddox, Kansas City, MO (US); Sara Boswell, Blue Springs, MO (US); Brian Libby, Kansas City, MO (US)

(73) Assignee: Cerner Innovation, Inc., Kansas City, KS (US)

( * ) Notice: Subject to any disclaimer, the term of this patent is extended or adjusted under 35 U.S.C. 154(b) by 145 days.

(21) Appl. No.: 13/529,258

(22) Filed: Jun. 21, 2012

(65) Prior Publication Data

US 2013/0346103 A1    Dec. 26, 2013

(51) Int. Cl.
*G06Q 50/22* (2012.01)
(52) U.S. Cl.
USPC .................................................. 705/2
(58) Field of Classification Search
USPC ............................................ 705/2–3
See application file for complete search history.

(56) References Cited

U.S. PATENT DOCUMENTS

| 5,991,731 | A * | 11/1999 | Colon et al. ................... 705/3 |
| 6,347,329 | B1 * | 2/2002 | Evans ......................... 709/202 |
| 7,054,823 | B1 * | 5/2006 | Briegs et al. ................... 705/2 |
| 8,032,545 | B2 * | 10/2011 | Setimi ......................... 707/769 |
| 2007/0143146 | A1 * | 6/2007 | Abraham-Fuchs et al. ...... 705/3 |
| 2007/0294110 | A1 * | 12/2007 | Settimi ......................... 705/3 |
| 2007/0294111 | A1 * | 12/2007 | Settimi ......................... 705/3 |
| 2008/0010254 | A1 * | 1/2008 | Settimi ......................... 707/3 |
| 2013/0332190 | A1 * | 12/2013 | Hoffman et al. ................... 705/3 |
| 2013/0332191 | A1 * | 12/2013 | Hoffman et al. ................... 705/3 |

* cited by examiner

*Primary Examiner* — Michael Fuelling
(74) *Attorney, Agent, or Firm* — Shook Hardy & Bacon LLP

(57) ABSTRACT

Methods, computer systems, and computer storage media are provided for providing a third-party user HIPAA-compliant access to an electronic medical record system at a clinical site. A request for a clinical study participant list is received from the third-party user, and it is determined that the third-party user has viewing and access rights with respect to the clinical study participant list. The third-party user can select a participant on the clinical study participant list and access the participant's electronic medical record within the electronic medical record system. The electronic medical record is presented to the third-party user in a read-only view, and the third-party user is prevented from searching the EMR system for other electronic medical records.

6 Claims, 11 Drawing Sheets

TASK VIEW HELP

ALL PATIENTS ENROLLED    PATIENT COUNT: 6

| | LAST NAME | FIRST NAME | MRN | | ENROLLMENT ID | ON STUDY | OFF TREATMENT | OFF STUDY | AMENDMENT |
|---|---|---|---|---|---|---|---|---|---|
| ALL PROTOCOLS | COOK | OLIVER | 11010 | - BW MRN | ML9673-00001 | 8/29/2011 | | | INITIAL PROTOCOL |
| ACT | DOWNS | MIKE | 9382 | - BW MRN | ML9673-00005 | 8/29/2011 | | | INITIAL PROTOCOL |
| HEMATOLOGY | JENKINS | KAYLA | 7842 | - BW MRN | ML9673-00002 | 8/29/2011 | | | INITIAL PROTOCOL |
| IMMUNOLOGY | LOWE | MARK | 7863 | - BW MRN | ML9673-00003 | 8/29/2011 | | | INITIAL PROTOCOL |
| LEUKEMIA/LYMPH... | MCGEE | ERIC | 7823 | - BW MRN | ML9673-00004 | 8/29/2011 | | | INITIAL PROTOCOL |
| RESEARCH NETW... | STEVENSON | ANNA | 9732 | - BW MRN | ML9673-00006 | 8/29/2011 | | | INITIAL PROTOCOL |
| SOLID TUMOR | | | | | | | | | |
| TRANSPLANTATIO... | | | | | | | | | |
| OTHER | | | | | | | | | |

- ACCREGISTRY
- AK325
- ASTGNA103
- CAD3002
- CAP2008
- COPD426
- DIAB457
- ECOG 2339 CER...
- EXERCISE STU...
- HT997
- IDC HT997
- LUNG
- ML9673  ← 412
- MOCK628
- PEDSD2009
- PEDVAC4001
- PPI3003
- REHAB3015
- SWOG 0421 CE...

HIPAA-COMPLIANT THIRD PARTY ACCESS TO ELECTRONIC MEDICAL RECORDS

BACKGROUND

Clinical trials are a necessary part of medical research and drug development. In fact, they are mandated by the Federal Drug and Safety Administration (FDA) as a necessary step along the path to FDA approval. The clinical trials are conducted to capture safety and efficacy data for health interventions including drugs, diagnostics, devices, and therapy protocols. Clinical trials can range from pilot studies with a small number of participants to very large studies with thousands of participants. Further, a single clinical trial can take place at one clinical site or may be spread across multiple clinical sites in different countries. Clinical trials are sponsored by the company seeking approval of the health intervention but may be managed by a contract research organization or a clinical trial unit in an academic center. These companies use clinical study auditors or monitors to provide oversight of the clinical study.

Ethical and regulatory guidelines surrounding human subject research in clinical trials require that clinical study monitors be given access to the medical records of clinical study participants to ensure that research documentation carried out at the clinical trial sites is an accurate and complete reflection of information actually documented in the participants' medical records. However, to maintain compliance with patient privacy standards set forth in the Health Insurance Portability and Accountability Act (HIPAA), clinical sites must ensure that clinical study monitors only access the medical records of patients who are actually participating in the clinical study, and the clinical sites must prevent access to medical records of patients who are not participating in the clinical study.

For clinical sites who utilize electronic medical record systems to store electronic medical records (EMRs) of patients, prior solutions to this problem have been both time and labor intensive. Solutions include printing the medical records of participants enrolled in a designated clinical study prior to an on-site visit by the clinical study monitor. This labor-intensive solution introduces a privacy risk in that the printed medical record must be appropriately controlled and destroyed after the visit.

Another solution requires the technical support staff at the clinical site to provide monitor-specific access to specified participants' electronic medical records for a specific time period. This must be done for each clinical study being conducted at the clinical site and must be done each time a monitor visits the site. This solution consumes valuable technical support resources. Yet another labor-intensive solution is to physically monitor access to participants' medical records by having a clinical site employee sit with the monitor as the monitor reviews a participant's electronic medical record. This helps to ensure that the monitor does not view other non-participant medical records.

There are also disadvantages to the current system from a clinical study monitor's perspective. For example, current solutions require that the monitor physically visit each clinical site which drives up the costs of research and development for the companies sponsoring the clinical trials. There is currently no safe or effective way for the clinical study monitor to remotely access the needed information.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The present invention is defined by the claims.

In brief and at a high level, this disclosure describes, among other things, methods, systems, and computer storage media for providing a clinical study monitor HIPAA-compliant access to an electronic medical record system at a clinical site. A clinical study participant list for a clinical study is generated and is presented to a third-party user upon determining that the third-party user has viewing and access rights related to the clinical study participant list. The clinical monitor can directly access a participant's EMR from the clinical study participant list. The participant's EMR is presented in a read-only mode and cannot be modified by the clinical monitor. Further, while viewing the participant's EMR, the clinical monitor is prevented from accessing EMRs of other patients not on the clinical study participant list.

BRIEF DESCRIPTION OF THE DRAWINGS

Embodiments are described in detail below with reference to the attached drawing figures, wherein:

FIG. 4 depicts an exemplary graphical user interface illustrating a clinical study participant list according to an embodiment of the present invention;

FIG. 5 depicts an exemplary graphical user interface illustrating a message presented to the third-party user when the third-party user is denied access to a clinical study participant list according to an embodiment of the present invention;

DETAILED DESCRIPTION

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

Embodiments of the present invention are directed to methods, computer systems, and computing storage media for providing a clinical study monitor HIPAA-compliant access to an electronic medical record system at a clinical site. A clinical study participant list for a clinical study is generated and is presented to a third-party user upon determining that the third-party user has viewing and access rights related to the clinical study participant list. The clinical monitor can directly access a participant's EMR from the clinical study participant list. The participant's EMR is presented in a read-only mode and cannot be modified by the clinical monitor. Further, while viewing the participant's EMR, the clinical monitor is prevented from accessing EMRs of other patients not on the clinical study participant list.

Figure 1:
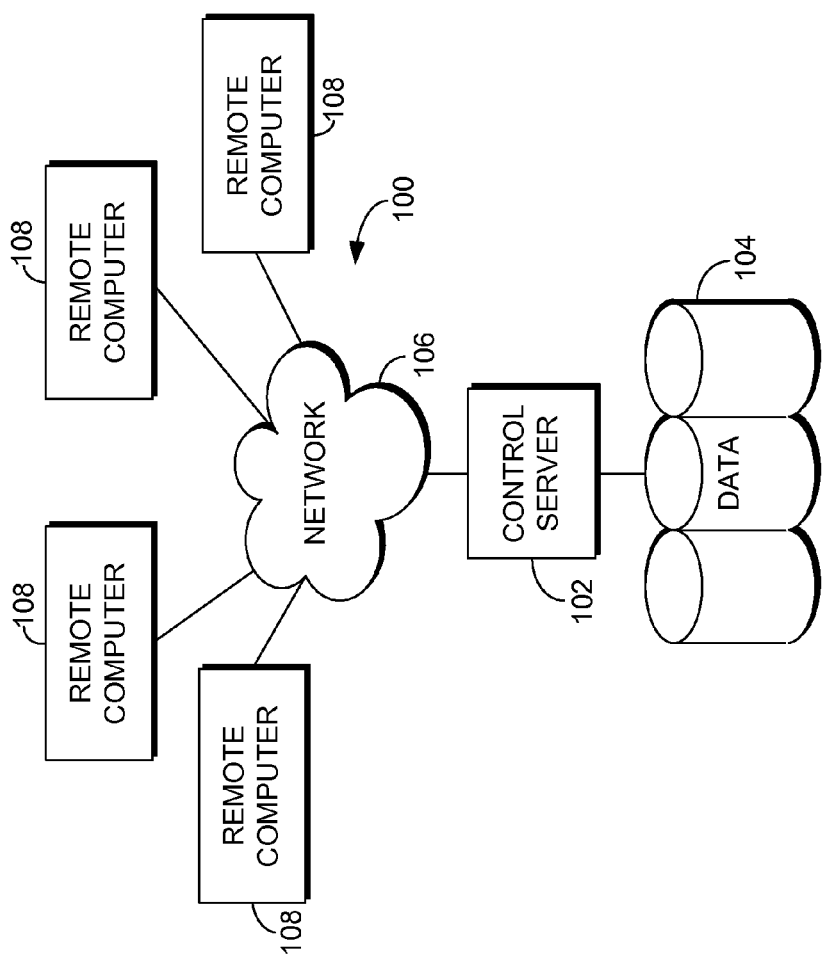
FIG. 1 is a block diagram of an exemplary computing environment suitable to implement embodiments of the present invention.

An exemplary computing environment suitable for use in implementing embodiments of the present invention is described below. FIG. 1 is an exemplary computing environment (e.g., medical-information computing-system environment) with which embodiments of the present invention may be implemented. The computing environment is illustrated and designated generally as reference numeral 100. The computing environment 100 is merely an example of one suitable computing environment and is not intended to suggest any limitation as to the scope of use or functionality of the invention. Neither should the computing environment 100 be interpreted as having any dependency or requirement relating to any single component or combination of components illustrated therein.

The present invention might be operational with numerous other purpose computing system environments or configurations. Examples of well-known computing systems, environments, and/or configurations that might be suitable for use with the present invention include personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

The present invention might be described in the general context of computer-executable instructions, such as program modules, being executed by a computer. Exemplary program modules comprise routines, programs, objects, components, and data structures that perform particular tasks or implement particular abstract data types. The present invention might be practiced in distributed computing environments where tasks are performed by remote processing devices that are linked through a communications network. In a distributed computing environment, program modules might be located in association with local and/or remote computer storage media (e.g., memory storage devices).

With continued reference to FIG. 1, the computing environment 100 comprises a computing device in the form of a control server 102. Exemplary components of the control server 102 comprise a processing unit, internal system memory, and a suitable system bus for coupling various system components, including data store 104, with the control server 102. The system bus might be any of several types of bus structures, including a memory bus or memory controller, a peripheral bus, and a local bus, using any of a variety of bus architectures. Exemplary architectures comprise Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The control server 102 typically includes therein, or has access to, a variety of computer-readable media. Computer-readable media can be any available media that might be accessed by control server 102, and includes volatile and nonvolatile media, as well as, removable and nonremovable media. By way of example, and not limitation, computer-readable media may comprise computer storage media and communication media. Computer storage media includes both volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by control server 102. Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer-readable media.

The control server 102 might operate in a computer network 106 using logical connections to one or more remote computers 108. Remote computers 108 might be located at a variety of locations in a medical or research environment, including clinical laboratories (e.g., molecular diagnostic laboratories), hospitals and other inpatient settings, veterinary environments, ambulatory settings, medical billing and financial offices, hospital administration settings, home healthcare environments, and clinicians' offices. Clinicians may comprise a treating physician or physicians; specialists such as surgeons, radiologists, cardiologists, and oncologists; emergency medical technicians; physicians' assistants; nurse practitioners; nurses; nurses' aides; pharmacists; dieticians; microbiologists; laboratory experts; laboratory technologists; genetic counselors; researchers; veterinarians; students; and the like. The remote computers 108 might also be physically located in nontraditional medical care environments so that the entire healthcare community might be capable of integration on the network. The remote computers 108 might be personal computers, servers, routers, network PCs, peer devices, other common network nodes, or the like and might comprise some or all of the elements described above in relation to the control server 102. The devices can be personal digital assistants or other like devices.

Computer networks 106 comprise local area networks (LANs) and/or wide area networks (WANs). Such networking environments are commonplace in offices, enterprise-wide computer networks, intranets, and the Internet. When utilized in a WAN networking environment, the control server 102 might comprise a modem or other means for establishing communications over the WAN, such as the Internet. In a networking environment, program modules or portions thereof might be stored in association with the control server 102, the data store 104, or any of the remote computers 108. For example, various application programs may reside on the memory associated with any one or more of the remote computers 108. It will be appreciated by those of ordinary skill in the art that the network connections shown are exemplary and other means of establishing a communications link between the computers (e.g., control server 102 and remote computers 108) might be utilized.

In operation, an organization might enter commands and information into the control server 102 or convey the commands and information to the control server 102 via one or more of the remote computers 108 through input devices, such as a keyboard, a pointing device (commonly referred to as a mouse), a trackball, or a touch pad. Other input devices comprise microphones, satellite dishes, scanners, or the like. Commands and information might also be sent directly from a remote healthcare device to the control server 102. In addition to a monitor, the control server 102 and/or remote computers 108 might comprise other peripheral output devices, such as speakers and a printer.

Although many other internal components of the control server 102 and the remote computers 108 are not shown, such components and their interconnection are well known. Accordingly, additional details concerning the internal construction of the control server 102 and the remote computers 108 are not further disclosed herein.

Figure 2:
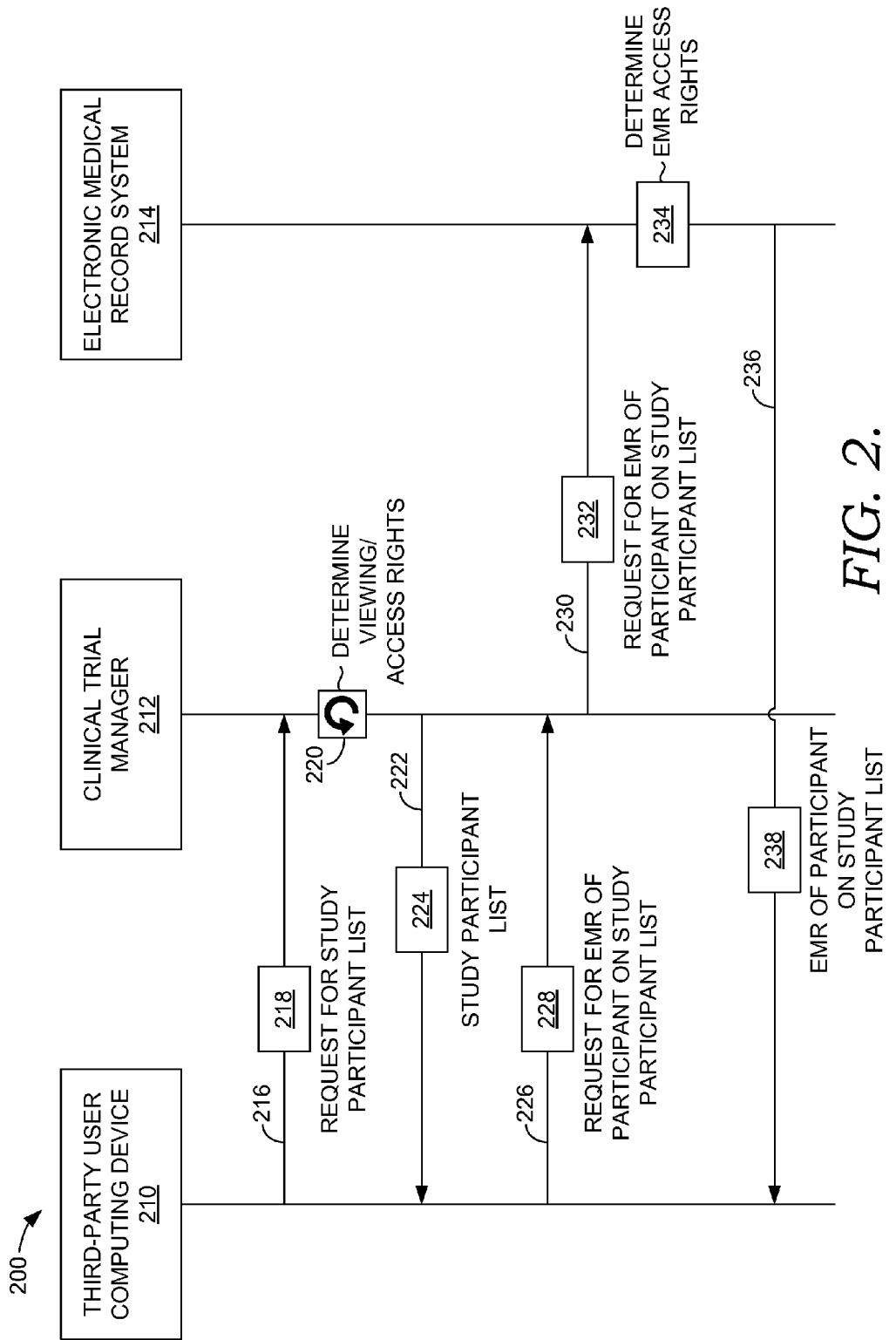
FIG. 2 depicts an illustrative process-flow diagram that depicts a method of providing a third-party user HIPAA-compliant access to an electronic medical record system at a clinical site according to an embodiment of the present invention.

Turning now to FIG. 2, a process-flow diagram, referenced generally by the numeral 200, is depicted illustrating a method of providing a third-party user HIPAA-compliant access to an electronic medical record system at a clinical site. Although aspects of the current invention are discussed in the context of a healthcare environment, it is contemplated that the principles set forth herein may also relate to other secure record systems that normally do not allow third-party users access to sensitive information stored in association with the record system. Such systems may include client records kept in association with, for example, law firms, educational institutions, or financial institutions.

FIG. 2 includes a third-party user computing device 210, a clinical trial manager 212, and an electronic medical record (EMR) system 214. The computing device 210, the clinical trial manager 212, and the EMR system 214 may all be in communication with one another via a network. The network may include, without limitation, one or more local area networks (LANs) and/or wide area networks (WANs). Such networking environments are commonplace in offices, enterprise-wide computer networks, intranets and the Internet. Accordingly, the network is not further described herein.

It should be understood that this and other arrangements described herein are set forth only as examples. Other arrangements and elements (e.g., machines, interfaces, functions, orders, and groupings of functions, etc.) can be used in addition to or instead of those shown, and some elements may be omitted altogether. Further, many of the elements described herein are functional entities that may be implemented as discrete or distributed components or in conjunction with other components/modules, and in any suitable combination and location. Various functions described herein as being performed by one or more entities may be carried out by hardware, firmware, and/or software. For instance, various functions may be carried out by a processor executing instructions stored in memory.

The third-party user computing device 210 may be any type of computing device. Such devices may include fixed, mobile, and portable devices including cellular telephones, personal digital assistants, tablet personal computers (tablet PCs), and devices such as the remote computer 108 of FIG. 1. The third-party computing device 210 may be at a location that is remote from a clinical site carrying out the clinical study. As used throughout this application, the term "third-party user" is meant to encompass any user who normally does not have access rights to an electronic medical record system associated with a clinical site. This typically includes users who are not associated in any way with the clinical site. For example, the user is not an employee of the clinical site and does not have privileges at the clinical site. In one aspect, the third-party user is a clinical monitor or auditor who is charged with ensuring that research documentation put forth by the clinical site is an accurate and complete reflection of information documented in the study participants' medical records. The clinical monitor is employed by, for example, the drug company sponsoring the clinical trial or by a clinical research organization running the clinical trial.

The clinical trial manager 212 is associated with one or more clinical sites and provides functionalities that enable management of one or more clinical studies carried out at the clinical sites. The clinical trial manager 212 dynamically creates and updates clinical study participant lists and presents the lists to approved personnel. As used throughout this application, the term "dynamically" means occurring in near real time. As well, the clinical trial manager 212 acts as a gateway to electronic medical records of participants on the clinical study participant lists. These functions will be explained in greater depth below.

The electronic medical record system 214 is associated with a clinical site. Clinical sites typically include healthcare facilities such as hospitals or clinics. These healthcare facilities have EMR systems that store EMRs of patients, including clinical trial participants. EMRs may comprise electronic clinical documents such as images, clinical notes, orders, summaries, reports, analyses, or other types of electronic medical documentation relevant to a particular patient's condition and/or treatment. Electronic clinical documents contain various types of information relevant to the condition and/or treatment of a particular patient and can include information relating to, for example, patient identification information, images, culture results, physical examinations, vital signs, past medical histories, surgical histories, family histories, histories of present illnesses, current and past medications, allergies, symptoms, past orders, completed orders, pending orders, tasks, lab results, other test results, patient encounters and/or visits, immunizations, physician comments, nurse comments, other caretaker comments, and a host of other relevant clinical information.

Continuing with respect to FIG. 2, at a step 216, a request 218 from the third-party user computing device 210 for a clinical study participant list is received by the clinical trial manager 212. The third-party user may initiate the request after submitting a set of authorization credentials and/or authentication credentials (e.g., a log-in name and password) on a log-in screen and being presented with a list of clinical studies.

At a step 220, the clinical trial manager 212 determines if the third-party user is authorized to view the clinical study participant list for the clinical trial based on, for example the set of authorization/authentication credentials. Further, the clinical trial manager 212 determines the third-party user's access rights with respect to the clinical study participant list based on, for example, the set of authorization/authentication credentials. Viewing and access rights for a clinical monitor may include the right to view a clinical study participant list and to access limited information about the participants on the list.

The viewing rights and the access rights may be determined based on a role associated with the authorization/authentication credentials such as a clinical monitoring or auditing role. In another aspect, the viewing and access rights may be determined based on the third-party user's identity as defined by the authorization/authentication credentials (i.e., the authorization/authentication credentials identify the user as "John Smith"). Viewing and access rights for the third-party user may be determined for more than one clinical study being conducted at a clinical site. For instance, a clinical site may be conducting 20 clinical studies for various drug companies. However, a clinical monitor working for Drug Company A may only have viewing and access rights to two of the clinical studies being sponsored by Drug Company A.

The clinical trial manager 212 is further configured to determine viewing and access rights for any number of users outside of those in a clinical monitoring role. For instance, the clinical trial manager 212 may determine viewing and access rights for personnel associated with a clinical study ranging from the principal investigator of the study to a nurse who administers a drug to one of the study participants. The rights for these personnel may include the right to create, act on, update, or view clinical study participant lists.

At a step 222, upon determining that the third-party user has viewing and access rights to the clinical study participant list, the clinical study participant list 224 is communicated to the third-party user computing device 210 and is presented on a user interface associated with the third-party computing device 210. The clinical study participant list 224 may include information such as patient name, enrollment ID, medical record number (MRN), and demographic information such as gender, ethnicity, and age. The clinical study participant list 224 may also include information detailing when the patient was enrolled in the study, if the patient is currently off treatment, and if the patient is no longer actively participating in the clinical study.

The third-party user is able to access additional information upon selecting a participant on the clinical study participant list 224. The additional information includes participant eligibility criteria and participant consent information. Participants who are enrolled in a clinical study are required to meet certain eligibility requirements that differ depending on the clinical study. The clinical monitor is able to access the participant's information as it pertains to the eligibility criteria and verify the participant's eligibility. Further, upon enrolling in a clinical study, study participants sign a consent form that gives the clinical monitor permission to view the participant's medical information as it pertains to the clinical study. The third-party user can access the consent form and verify that the participant has given proper consent.

Continuing with FIG. 2, at a step 226, a request 228 from the third-party user computing device 210 is received by the clinical trial manager 212. The request 228 is a request to view the electronic medical record (EMR) of a participant on the clinical study participant list 224; the EMR is stored in association with the EMR system 214. At a step 230, a request 232 for the EMR of the participant is communicated from the clinical trial manager 212 to the EMR system 214.

At a step 234, the EMR system 214 determines access rights of the third-party user based on the third-party user's role (i.e., clinical monitor). The access rights include enabling a read-only view of the participant's EMR and preventing any third-party user modifications to the participant's EMR. Further, the access rights include disabling the patient search capabilities typically associated with the EMR system 214. In one aspect, the access rights further include placing restrictions on the data within the participant's EMR that is available for viewing by the clinical monitor. For example, the data may be restricted to information pertaining solely to the clinical study. The EMR system 214 need only define the access rights for an auditor/monitor role one time. Any third-party user who is authenticated as a clinical monitor is given similar access rights.

At a step 236, the participant's EMR 238 is communicated to the third-party user computing device 210 and is presented on a user interface associated with the device 210. The third-party user is able to view information associated with the participant's EMR and verify that it matches research documentation information. However, the third-party user is prevented from searching for medical information of patients not participating in the clinical study, and, further, the third-party user is prevented from modifying any of the information in the participant's EMR. Once the third-party user has finished viewing information associated with the participant's EMR, the third-party user can select another participant on the clinical study participant list and view that participant's EMR. The result of the process flow 200 is that a clinical monitor can directly access a participant's EMR from a clinical study participant list. Further, the process flow 200 may be carried out using remote access obviating the need for the clinical monitor to physically visit the clinical site.

In one aspect, the clinical trial manager 212 is further configured to disable access rights for the third-party user after the monitoring/auditing session is complete. If the third-party user is scheduled to conduct another audit, the clinical trial manager 212 can enable access rights yet again. This adds an extra level of security to the participants' EMRs. Additionally, the clinical trial manager 212 can be configured to create an audit trail for the monitoring session. The audit trail provides information on clinical study participant lists accessed by the third-party user, and EMRs viewed by the third-party user.

Figure 3:
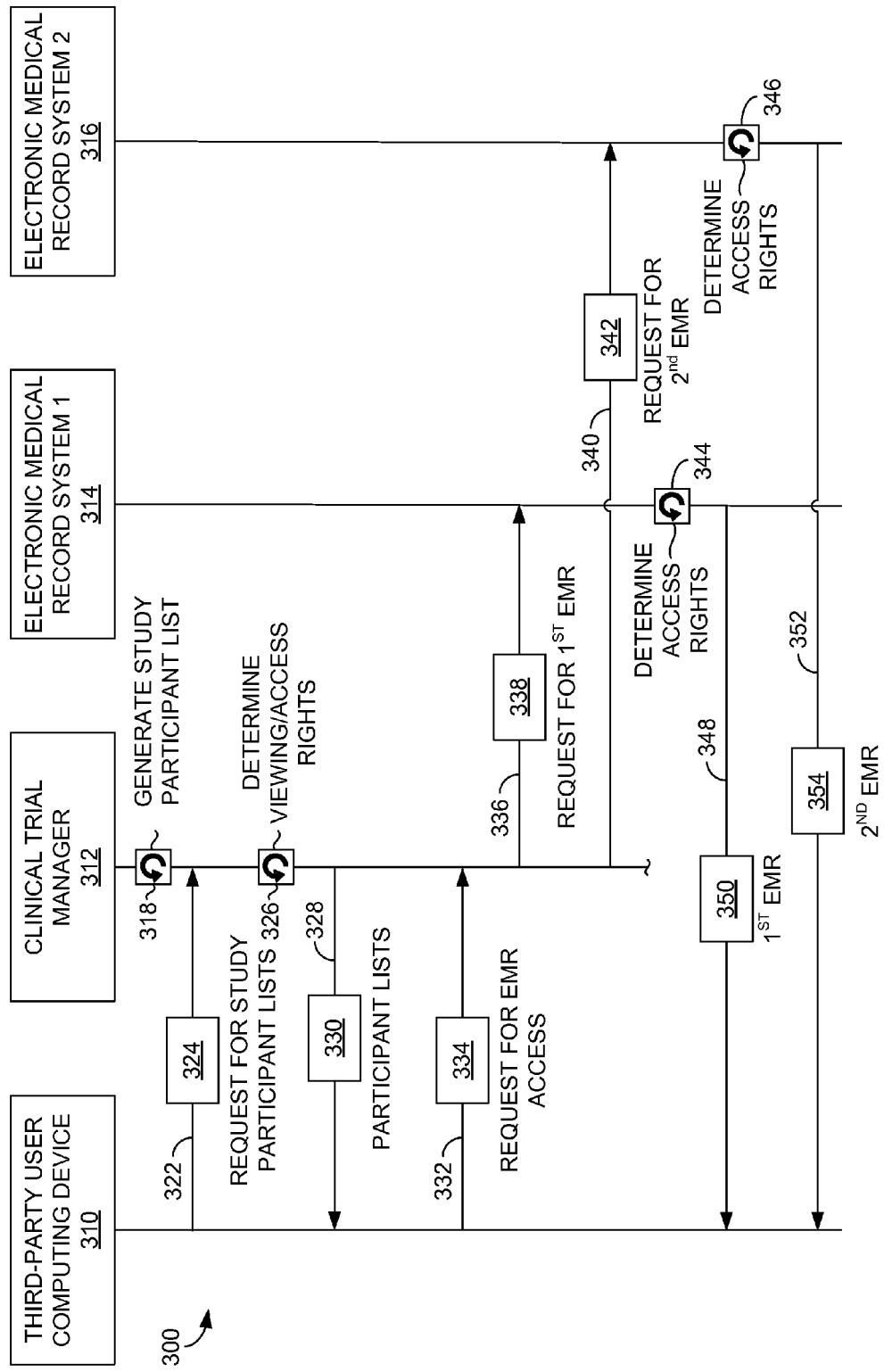
FIG. 3 depicts an illustrative process-flow diagram that depicts a method of dynamically creating one or more clinical study participant lists and providing a third-party user with HIPAA-compliant access to electronic medical records of participants on the clinical study participant lists according to an embodiment of the present invention.

Turning now to FIG. 3, a process-flow diagram, referenced generally by the numeral 300, is depicted illustrating a method of dynamically creating one or more clinical study participant lists and providing a third-party user with HIPAA-compliant access to electronic medical records of participants on the clinical study participant lists. FIG. 3 includes a third-party user computing device 310, a clinical trial manager 312, a first electronic medical record (EMR) system 314, and a second EMR system 316. The third-party user computing device 310 and the clinical trial manager 312 may be the same as the third-party user computing device 210 and the clinical trial manager 212 of FIG. 2. As well, some of the steps outlined in FIG. 3 correspond to the steps outlined in FIG. 2. As such, not as much detail will be included for these redundant steps.

The first EMR system 314 and the second EMR system 316 share similarities with the EMR system 214 of FIG. 2 in that each of the EMR systems 314 and 316 store electronic medical records of clinical study participants. However the first EMR system 314 and the second EMR system 316 in FIG. 3 may be in different geographical locations and may be associated with different clinical sites. For example, the first EMR system 314 may be associated with a first clinical site, and the second EMR system 316 may be associated with a second clinical site. In one aspect, the first and second clinical sites are conducting separate clinical studies. In a second aspect, the first and second clinical sites are conducting the same clinical study.

At a step 318, the clinical trial manager 312 generates a first clinical study participant list for a first clinical study being conducted at the first clinical site and generates a second clinical study participant list for a second clinical study being conducted at the second clinical site. The second clinical study may be a different clinical study than the first clinical study. Alternatively, the second clinical study may involve the same subject matter as the first clinical study with the difference being that it is being conducted at the second clinical site with a different group of study participants. The clinical study participant lists are created dynamically as changes and/or updates become available. As such, the clinical study participant lists reflect the latest information on participants who are actively involved in the clinical study. Participants are added to the clinical study participant lists upon determination by the clinical trial manager 312 that each participant meets eligibility requirements and has provided proper consent to be in the study. Participants are classified as "off study" on the clinical study participant lists upon determination by the clinical trial manager 312 that the party is no longer actively involved in the study.

At a step 322, a request 324 for the first and second clinical study participant lists is received by the clinical trial manager 312; the request 324 is communicated by the third-party user computing device 310. The request 324 may be received after a list of clinical studies is presented to the third-party user. Requests for multiple clinical study participant lists are common when a clinical monitor is charged with auditing multiple clinical studies. The request 324 for the first and second clinical study participant lists may be associated with a set of authorization/authentication credentials. The same set of authorization/authentication credentials may be used for both the first and second clinical study participant lists. Alternatively, different sets of authorization/authentication credentials may be used for the first and second clinical study participant lists.

At a step 326, the clinical trial manager 312 determines viewing rights and access rights associated with the set(s) of authorization/authentication credentials. Like above, the viewing and access rights may be based on a role (e.g., a clinical monitoring role) associated with the set of authorization/authentication credentials. Alternatively, the viewing and the access rights may be based on a user identity associated with the set of authorization/authentication credentials. Viewing rights for clinical monitors may include the right to view participant names, eligibility criteria, and consent information. Access rights may include the right to access EMRs of study participants.

At a step 328, the first and second clinical study participant lists 330 are communicated from the clinical trial manager 312 to the third-party user computing device 310. At a step 332, a request 334 for EMR access to one or more participants on the first and second clinical study participant lists 330 is received by the clinical trial manager 312. The request 334 may be initiated when the third-party user selects participants on the clinical study participant lists and indicates an intent to view the participants' EMRs. At a step 336, a request 338 for the EMR of a participant on the first clinical study participant list is communicated by the clinical trial manager 312 to the first EMR system 314. Further, at a step 340, a request 342 for the EMR of a participant on the second clinical study participant list is communicated by the clinical trial manager 312 to the second EMR system 316.

The first and second EMR systems 314 and 316 determine access rights associated with the requests at steps 344 and 346 respectively. As mentioned above, the first and second EMR systems 314 and 316 may have previously defined access rights for users in a clinical monitoring role. These access rights may be limited to read-only views of medical records. The access rights may prevent further patient searching by the clinical monitor and may prohibit any modifications to the electronic medical records by the clinical monitor.

At a step 348, the first EMR system 314 communicates EMR 350 of the participant on the first clinical study participant list to the third-party computing device 310, and, at a step 352, the second EMR system 316 communicates EMR 354 of the participant on the second clinical study participant list to the third-party computing device 310. The process-flow 300 illustrates how a clinical monitor can oversee multiple clinical trials at disparate clinical sites through the clinical trial manager 312. Further, the clinical trial manager 312 ensures that any medical records presented to the clinical monitor are done so in a HIPAA-compliant manner.

FIG. 4 depicts an exemplary graphical user interface (GUI) 400 illustrating a clinical study participant list. The GUI 400 includes a list of clinical trials 410 being managed by a clinical trial manager such as the clinical trial manager 312 of FIG. 3. The user (e.g., a clinical trial monitor) is able to select a clinical trial such as a clinical trial 412. Upon selecting the clinical trial 412, and after determining that the user has viewing and access rights, a clinical study participant list 414 is presented to the user; the clinical study participant list 414 corresponds to the clinical trial 412. The clinical study participant list 414 includes the participants' names, enrollment ID, medical record number (MRN), when they were enrolled in the study, and whether they are off treatment or off study. The amendment column of the clinical study participant list 414 is used to indicate whether there has been a change in the protocol, informed consent, or eligibility criteria.

Figure 5:
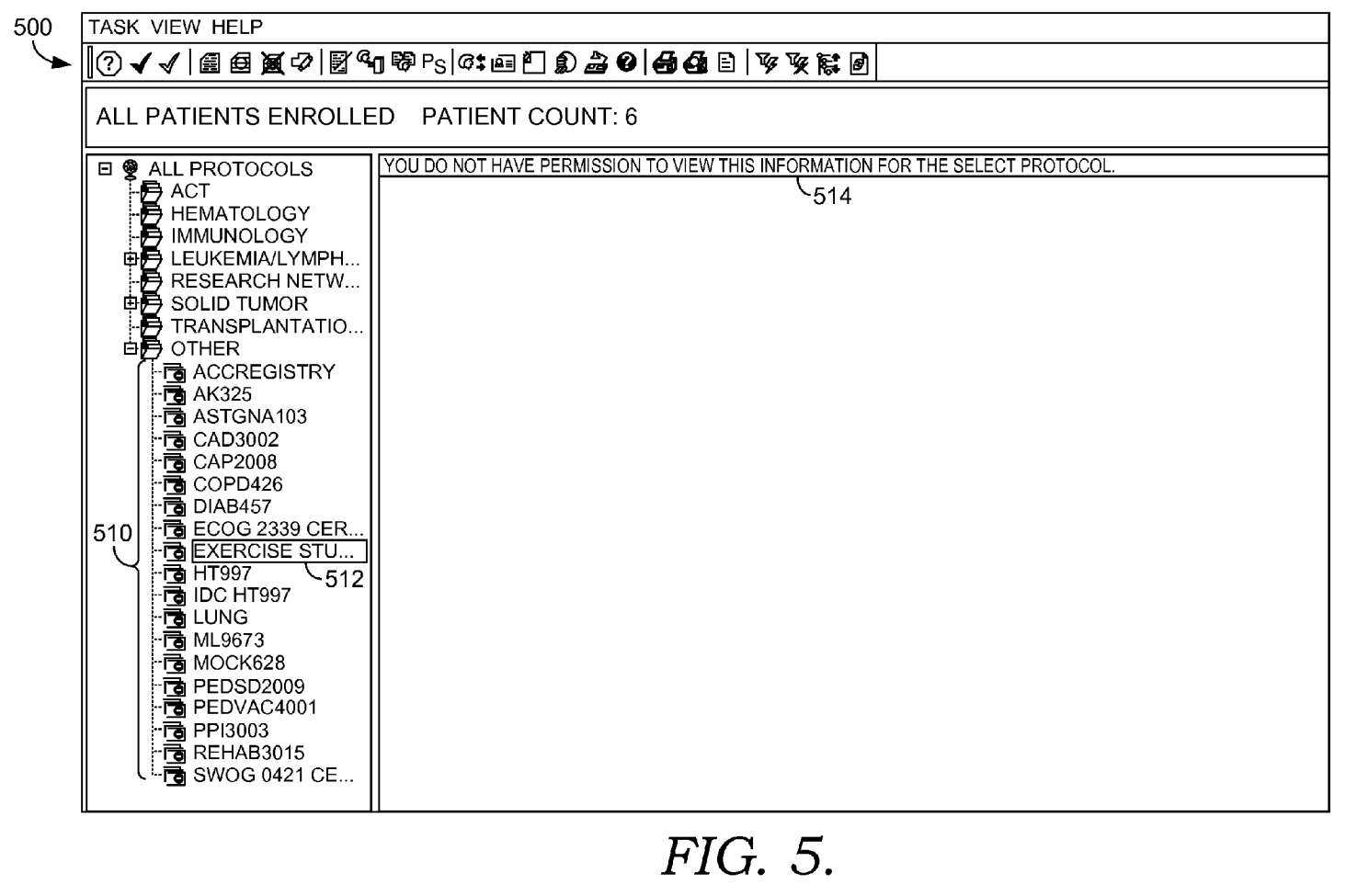

Turning to FIG. 5, FIG. 5 is an exemplary graphical user interface (GUI) 500 illustrating a message seen when a third-party user is denied viewing and access rights to a clinical study participant list. The GUI 500 includes a list of clinical trials 510 being managed by a clinical trial manager. The third-party user has attempted to access clinical study 512. However, upon determining that the third-party user does not have viewing and access rights to the clinical study 512, a message 514 is presented informing the user that the user does not have permission to view the clinical study participant list for the clinical study 512.

Figure 6:
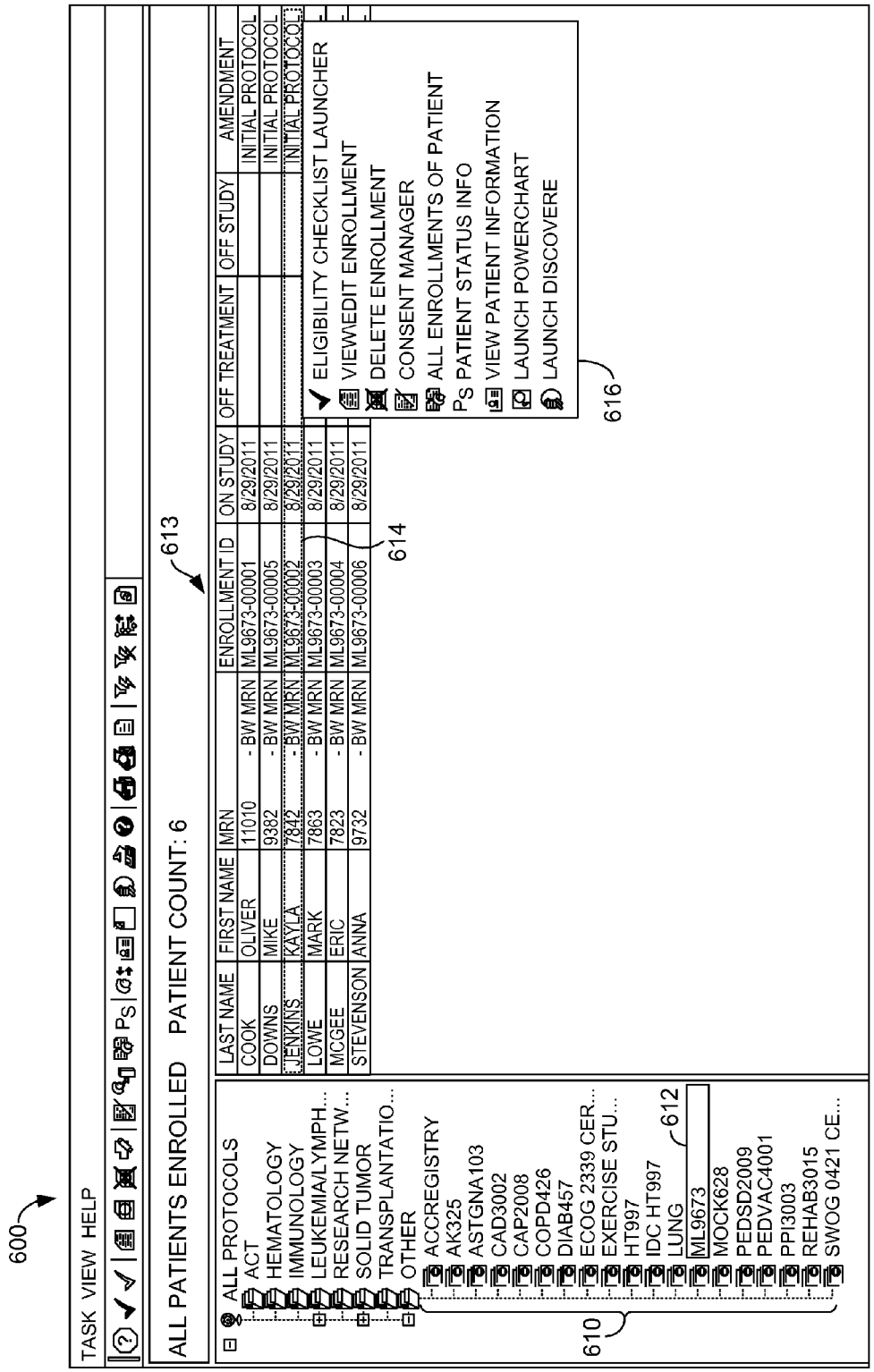
FIG. 6 depicts an exemplary graphical user interface illustrating various functionalities presented to a third-party user after accessing a clinical study participant list according to an embodiment of the present invention.

FIG. 6 depicts yet another exemplary graphical user interface (GUI) 600 illustrating various functionalities presented to a third-party user after accessing a clinical study participant list. The GUI 600 includes a list of clinical studies 610 currently being managed by a clinical trial manager. The third-party user has selected a clinical trial 612 and is presented with a clinical study participant list 613. Further, the third-party user has selected a participant 614 on the clinical study participant list 613. Upon selection of the participant 614, the third-party user is presented with a list of functionalities 616. The third-party user may be able to access some or all of the functionalities 616.

By accessing the list of functionalities 616, the third-party user can view eligibility criteria associated with the participant 614. As mentioned, each clinical study has its own set of eligibility requirements, and participants enrolled in the clinical study are expected to meet those eligibility requirements. By viewing eligibility criteria associated with the participant 614, the third-party user can verify that the participant 614 meets the necessary requirements.

The list of functionalities 616 also includes a consent manager. Selection of the consent manager initiates the presentation of the consent form of the participant 614. The participant must have a valid consent on file granting permission to the third-party clinical monitor to view the participant's medical records. The list of functionalities 616 further includes an option which enables the third-party user to directly access the participant's EMR from its associated EMR system. The third-party user is able to view information from the participant's EMR but cannot modify the information. Additionally, the third-party user is prevented from searching for other patients while viewing the patient's EMR. Although there are other functionalities presented in the list of functionalities 616, these functionalities may not be available to the third-party user. The unavailable functionalities may include "view/edit enrollment," "delete enrollment," and "all enrollment of patients." The unavailable functionalities may be indicated by graying out these options on the list of functionalities 616.

Figure 7A:
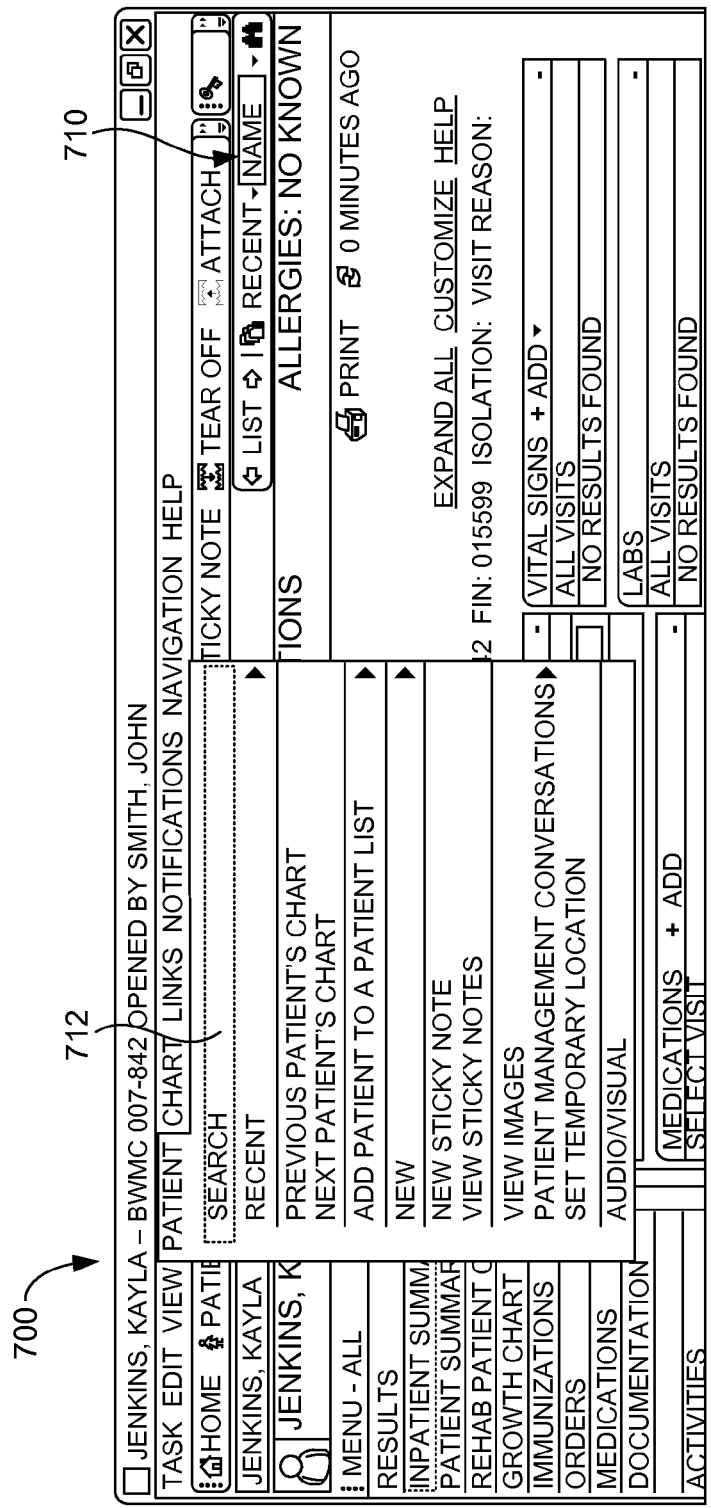
FIGS. 7A-7B depict exemplary graphical user interfaces of a participant's electronic medical record illustrating differing access rights according to an embodiment of the present invention.
Figure 7B:
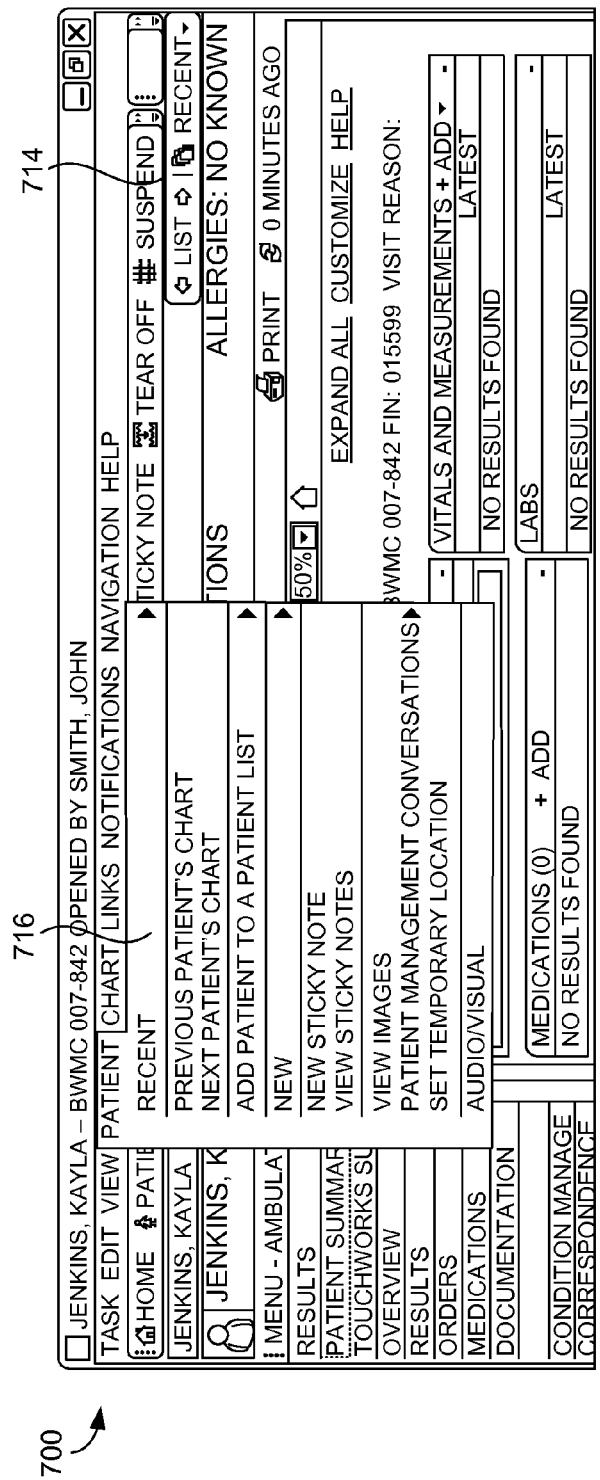

FIGS. 7A and 7B are two views of an exemplary graphical user interface (GUI) 700 illustrating differing access rights based on a user's role. FIG. 7A depicts a view of a participant's EMR that would be accessible to a user who is associated with the clinical site that is treating the participant. The user may be an employee at the clinical site and be involved in the participant's care (e.g., a nurse, therapist, social worker, etc.). As well, the user may be a physician who has privileges at the clinical site and is also involved in the participant's care. FIG. 7A illustrates functionalities that are commonly presented to these types of users. The functionalities include, for example, a patient search feature accessible in display area 710. The user is able to input a second participant's name in the search box of the display area 710 and directly access the second participant's EMR. The user can also search for patients who are not enrolled in the clinical study but are being treated at the clinical site using the display area 710. The user can also conduct patient searches using the display area 712, which has similar search features as that of the display area 710. Further, the user can input and/or modify values in the participant's EMR and can access additional information associated with the participant from the EMR.

By contrast, FIG. 7B depicts a view of a participant's EMR that would be presented to a third-party user in a clinical monitoring role. As can be seen, the display area 710 of FIG. 7A has been replaced with display area 714. The display area 714 does not allow the third-party user to search for EMRs of other participants or patients. Instead, the third-party user accesses additional EMRs of participants by selecting them on the clinical study participant list. As well, the display area 712 of FIG. 7A has been replaced with display area 716 which also prevents the third-party user from searching for EMRs while working within the context of the EMR system. The third-party user has read-only access to the GUI 700 in FIG. 7B and cannot modify any of the presented information.

Figure 8:
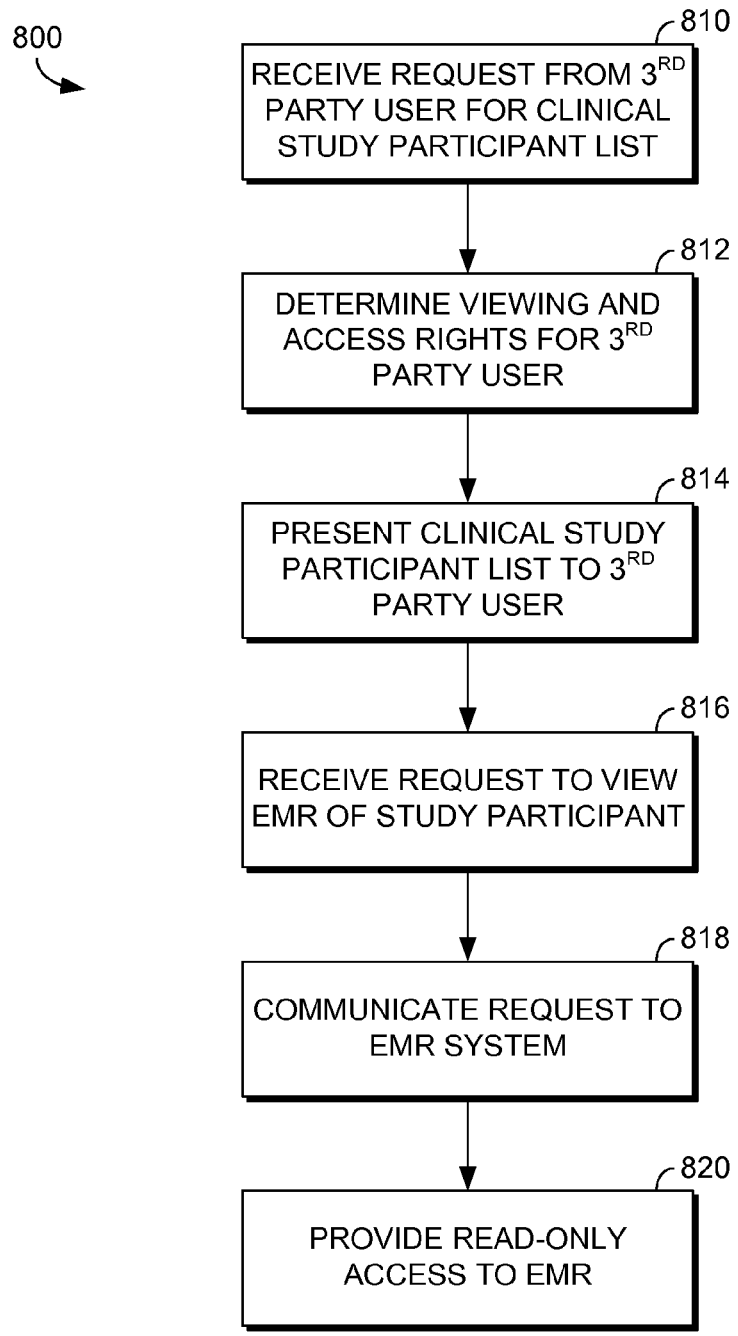
FIG. 8 depicts a flow diagram illustrating a method of providing a third-party user HIPAA-compliant access to an electronic medical record system at a clinical site according to an embodiment of the present invention.

Turning to FIG. 8, FIG. 8 is a flow diagram of an exemplary method 800 of providing a third-party user HIPAA-compliant access to an electronic medical record system at a clinical site. At a step 810, a request from the third-party user for a clinical study participant list is received by, for example, a clinical trial manager such as the clinical trial manager 212 of FIG. 2. The request for the clinical study participant list may be received from a computing device that is at a remote location from the clinical site. The request for the clinical study participant list may be received subsequent to presenting the third-party user with a list of clinical studies being conducted at the clinical site. Further, the request may be associated with a set of authorization and/or authentication credentials.

At a step 812, viewing and access rights are determined for the third-party user based on, for example, the set of authorization/authentication credentials. In one aspect, the authorization/authentication credentials may indicate that the third-party user is in a clinical monitoring role for a specified clinical study. In another aspect, the authorization/authentication credentials may identify the third-party user as an individual who has certain viewing and access rights. The viewing and access rights for a clinical monitor include the right to view the clinical study participant list associated with the clinical study being audited by the clinical monitor and the right to access one or more electronic medical records of participants on the clinical study participant list.

At a step 814, after determining that the third-party user has viewing and access rights, the clinical study participant list is presented to the third-party user. The clinical study participant list represents an up-to-date list of participants actively involved in the clinical study. If it is determined at step 812, that the third-party user does not have viewing and access rights to the clinical study participant list, a message is presented to the third-party user apprising him or her of this information.

At a step 816, a request from the third-party user to view an electronic medical record of one of the participants on the clinical study participant list is received. The electronic medical record is stored in association with an EMR system at the clinical site. The request may be received from a computing device that is located remote from the clinical site. Additional requests may include a request to view eligibility criteria for a participant or to view consent information of a participant.

At a step 818, the request to access the EMR of a participant is communicated to the EMR system at the clinical site. After verification by the EMR system that the third-party user is in a clinical monitoring role, the third-party user is given access to the participant's EMR at a step 820. The access is limited to a read-only view. Further, the third-party user is prevented from searching the EMR system for the EMRs of other participants on the clinical study participant list or for EMRs of patients being cared for at the clinical site. The third-party user may also be given access to only a limited portion of the participant's EMR.

In additional aspects, viewing and access rights may be disabled for the third-party user after the clinical monitoring session is complete. As well, an audit trail may be created that indicates the clinical study participant lists viewed by the third-party user and the EMRs accessed by the third-party user.

Figure 9:
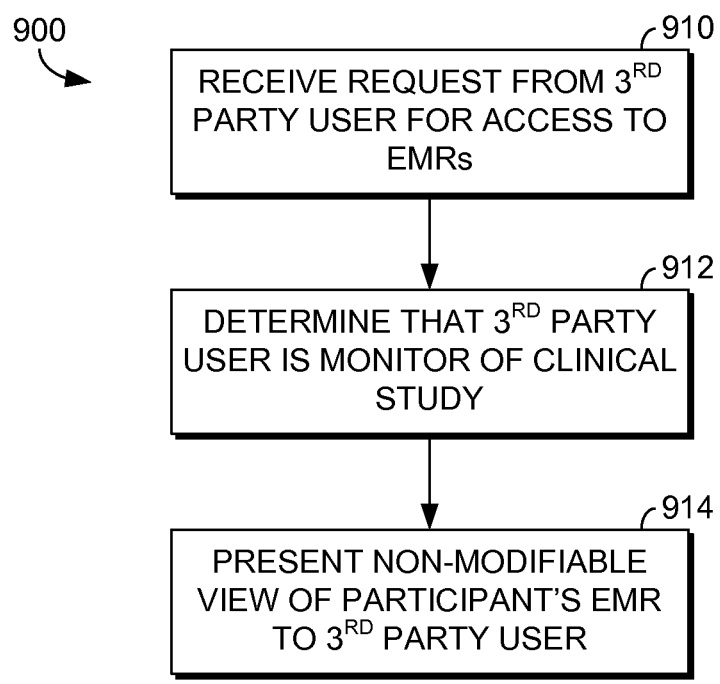
FIG. 9 depicts a flow diagram illustrating a method of permitting a third-party user access to electronic medical records stored in association with an electronic medical record system of a clinical site in order to conduct a clinical monitoring session according to an embodiment of the present invention.

FIG. 9 depicts a flow diagram of an exemplary method 900 of permitting a third-party user access to electronic medical records stored in association with an electronic medical record system of a clinical site in order to conduct a clinical auditing session. The method 900 is carried out by the EMR system at the clinical site. At a step 910, a request is received from the third-party user for access to one or more electronic medical records stored in association with the EMR system; the third-party user is not associated with the clinical site (i.e., the third-party user is not employed by the clinical site and does not have privileges at the clinical site). The request may be communicated by a clinical trial manager such as the clinical trial manager 212 of FIG. 2. Further, the request may be associated with a set of authorization/authentication credentials.

At a step 912, it is determined that the third-party user is in a clinical monitoring role. This determination may be based on the set of authorization/authentication credentials. In one aspect, the EMR system predetermines the access rights of users in a clinical monitoring role. Thus, once a third-party user is identified as a clinical monitor, a defined set of access rights with respect to electronic medical records are enabled. The access rights may include presenting a read-only view of a participant's EMR, preventing modification of data in the EMR, and preventing the third-party user from accessing any search functions associated with the EMR system. Further, access rights may include presenting only a limited portion of the information in the participant's EMR. At a step 914, a non-modifiable view of the participant's EMR is presented to the third-party user.

Figure 10:
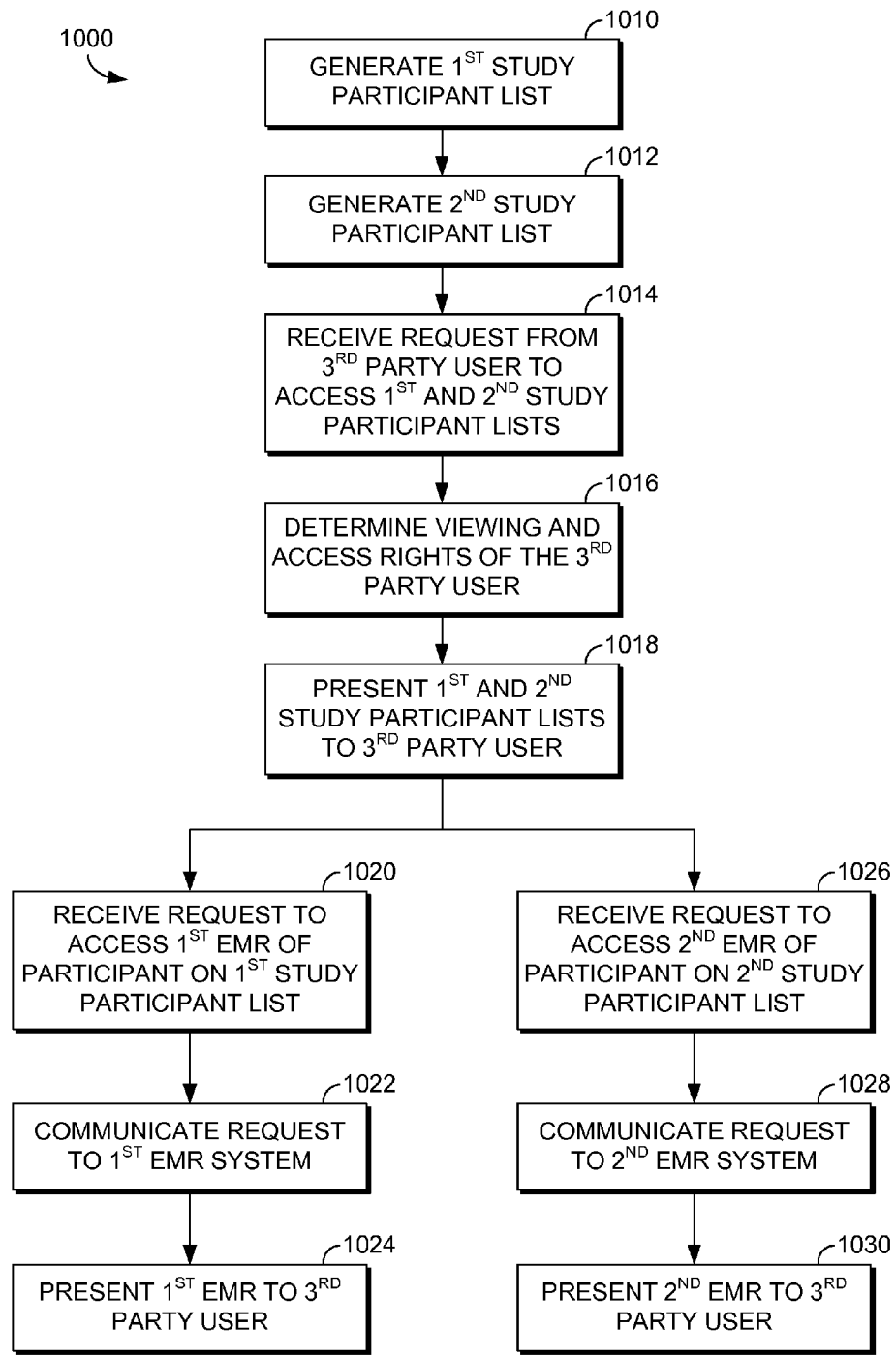
FIG. 10 depicts a flow diagram illustrating a method of dynamically creating one or more clinical study participant lists and providing a third-party user with HIPAA-compliant access to electronic medical records of participants on the clinical study participants lists according to an embodiment of the present invention.

FIG. 10 depicts a flow diagram of an exemplary method 1000 of dynamically creating one or more clinical study participant lists and providing a third-party user with HIPAA-compliant access to electronic medical records of participants on the clinical study participant lists. At a step 1010 and at a step 1012, first and second clinical study participant lists are generated by a clinical trial manager such as the clinical trial manager 312 of FIG. 3. The first clinical study participant list corresponds to a first clinical study being conducted at a first clinical site, and the second clinical study participant list corresponds to a second clinical study being conducted at a second clinical site. The first and second clinical sites may maintain disparate EMR systems and be located remotely from each other. The first clinical study may involve the same subject matter as the second clinical study or it may involve different subject matter.

The first and second clinical study participant lists are generated by identifying a set of patients who have enrolled in a clinical study (e.g., the first or second clinical study) and determining that the set of patients meets participant eligibility requirements for the clinical study and that the set of patients meets consent requirements. The first and second clinical study participant lists are generated in near real time and reflect up-to-date participant information.

At a step 1014, a request to access the first and second clinical study participant lists is received from the third-party user, and, at a step 1016, viewing and access rights are determined for the third-party user. The viewing and access rights may be the same or different for each of the clinical study participant lists. Based on the viewing and access rights determined at step 1016, the first and second clinical study participant lists are presented to the third-party user at a step 1018.

At a step 1020, a request is received from the third-party user to access an EMR of a first participant on the first clinical study participant list. The request may be initiated subsequent to the third-party user selecting a participant on the first clinical study participant list and indicating a desire to view the participant's EMR. At a step 1022, the request to view the EMR is communicated to the EMR system at the first clinical site. Upon verification by the EMR system that the third-party user is in a clinical monitoring role, the EMR of the first participant is presented to the third-party user in a non-modifiable view at a step 1024.

Similarly, at a step 1026, a request is received from the third-party user to access an EMR of a participant on the second clinical study participant list. At a step 1028, the request is communicated to the EMR system at the second clinical site, and, upon verification by the EMR system that the third-party user is in a clinical monitoring role, the EMR is presented to the third-party user in a non-modifiable view at a step 1030.

The present invention has been described in relation to particular embodiments, which are intended in all respects to be illustrative rather than restrictive. Further, the present invention is not limited to these embodiments, but variations and modifications may be made without departing from the scope of the present invention.

What is claimed is:

1. One or more non-transitory computer readable media having computer-executable instructions embodied thereon that, when executed, cause a computing device to perform a method of providing an auditor of a clinical study being conducted at a clinical site access to electronic medical records (EMRs) of participants in the clinical study, wherein the clinical study participants' EMRs are stored in association with an EMR system at the clinical site, the method comprising:

receiving a request from the auditor to view a clinical study participant list for the clinical study being conducted at the clinical site, the request including a set of authorization and authentication credentials, wherein the auditor is unaffiliated with the clinical site, and wherein the auditor is responsible for ensuring that documentation provided by the clinical site regarding the clinical study is a complete and accurate reflection of information contained in the clinical study participants' EMRs;

based on the set of authorization and authentication credentials, determining that the auditor is authorized to view the clinical study participant list for the clinical study;

presenting the clinical study participant list to the auditor;

receiving a request from the auditor to view one or more electronic medical records (EMRs) of one or more participants on the clinical study participant list, wherein the auditor does not normally have viewing rights to the one or more EMRs of the one or more participants because the auditor is unaffiliated with the clinical site;

communicating the request to the EMR system at the clinical site, wherein upon receipt of the request, the EMR system determines that the auditor is authorized to view the one or more EMRs of the one or more participants;

incident to communicating the request to the EMR system at the clinical site, receiving from the EMR system at the clinical site the one or more EMRs of the one or more participants in the clinical study; and presenting on a user interface associated with the auditor a read-only view of only to the one or more EMRs of the one or more participants of the clinical study.

2. The media of claim 1, wherein the one or more participants have previously authorized EMR access to auditors associated with clinical studies in which the one or more participants are enrolled.

3. The media of claim 1, wherein the clinical study participant list is continually updated as new participants are enrolled in the clinical study.

4. The media of claim 1, wherein the request to view the clinical study participant list is received from the auditor while the auditor is at a location remote from the clinical site.

5. The media of claim 1, wherein the read-only view to the one or more EMRs of the one or more participants of the clinical study is limited to a predetermined portion of the one or more EMRs of the one or more participants.

6. The media of claim 1, further comprising:
   creating an audit trail documenting the auditor's access to the one or more EMRs of the one or more participants.

* * * * *